(12) United States Patent
Misslitz et al.

(10) Patent No.: US 6,410,485 B1
(45) Date of Patent: Jun. 25, 2002

(54) SACCHARIN-5-CARBONYL DERIVATIVES WITH HERBICIDAL EFFECT

(75) Inventors: Ulf Misslitz, Neustadt; Ernst Baumann, Dudenhofen; Wolfgang von Deyn, Neustadt; Steffen Kudis, Mannheim; Klaus Langemann, Worms; Guido Mayer, Neustadt; Ulf Neidlein, Mannheim; Matthias Witschel, Ludwigshafen; Roland Götz, Neulussheim; Michael Rack, Heidelberg; Peter Plath, Frankenthal; Martina Otten, Ludwigshafen; Karl-Otto Westphalen, Speyer; Helmut Walter, Obrigheim, all of (DE)

(73) Assignee: BASF Aktiengesellschaft, Ludwigshafen (DE)

(*) Notice: Subject to any disclaimer, the term of this patent is extended or adjusted under 35 U.S.C. 154(b) by 0 days.

(21) Appl. No.: 09/914,797
(22) PCT Filed: Feb. 21, 2000
(86) PCT No.: PCT/EP00/01408
§ 371 (c)(1), (2), (4) Date: Sep. 5, 2001
(87) PCT Pub. No.: WO00/53590
PCT Pub. Date: Sep. 14, 2000

(30) Foreign Application Priority Data

Mar. 5, 1999 (DE) .......................... 199 09 645

(51) Int. Cl.$^7$ .................. A01N 43/80; A61K 31/428; C07D 275/06
(52) U.S. Cl. .................. 504/269; 514/373; 548/210; 548/211
(58) Field of Search ................ 548/210, 211; 514/373; 504/269

(56) References Cited

U.S. PATENT DOCUMENTS

| 5,744,425 A | 4/1998 | Plath et al. ............ 504/269 |
| 5,801,120 A | 9/1998 | Lee et al. ............. 504/236 |

FOREIGN PATENT DOCUMENTS

| WO | 96/05182 | 2/1996 |
| WO | 96/22957 | 8/1996 |

*Primary Examiner*—Laura L. Stockton
(74) *Attorney, Agent, or Firm*—Keil & Weinkauf

(57) ABSTRACT

The present application relates to saccharin-5-carbonyl derivatives of the formula I

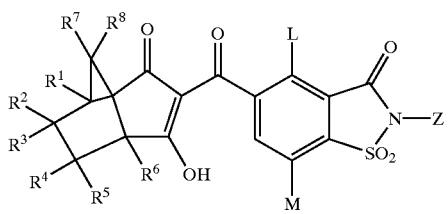

in which the substituents have the following meanings:

L is $C_1$–$C_6$-alkyl, $C_1$–$C_6$-alkoxy;

Z is $C_1$–$C_6$-alkyl, $C_3$–$C_8$-cycloalkyl, $C_3$–$C_6$-alkenyl, $C_3$–$C_5$-alkynyl, phenyl-$C_1$–$C_6$-alkyl or phenyl, where the phenyl rings are in each case optionally mono- or polysubstituted by $C_1$–$C_6$-alkyl, $C_1$–$C_6$-alkoxy or halogen;

M is hydrogen, $C_1$–$C_6$-alkyl, $C_1$–$C_6$-alkoxy, halogen, cyano, nitro or halo-$C_1$–$C_6$-alkyl;

$R^1$, $R^2$, $R^3$, $R^4$, $R^5$, $R^6$, $R^7$, $R^8$ are hydrogen, $C_1$–$C_6$-alkyl;

and agriculturally utilizable salts of the compound I.

15 Claims, No Drawings

SACCHARIN-5-CARBONYL DERIVATIVES WITH HERBICIDAL EFFECT

This application is a 371 of PCT/EP00/01408 filed Feb. 21, 2000.

The present application relates to saccharin-5-carbonyl derivatives of the formula I

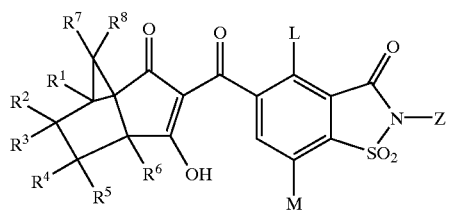

in which the substituents have the following meanings:

L is $C_1$–$C_6$-alkyl, $C_1$–$C_6$-alkoxy;

Z is $C_1$–$C_6$-alkyl, $C_3$–$C_8$-cycloalkyl, $C_3$–$C_6$-alkenyl, $C_3$–$C_5$-alkynyl, phenyl-$C_1$–$C_6$-alkyl or phenyl, where the phenyl rings can be mono- or polysubstituted by $C_1$–$C_6$-alkyl, $C_1$–$C_6$-alkoxy and halogen;

M is hydrogen, $C_1$–$C_6$-alkyl, $C_1$–$C_6$-alkoxy, halogen, cyano, nitro or halo-$C_1$–$C_6$-alkyl;

$R^1, R^2, R^3, R^4, R^5, R^6, R^7, R^8$ are hydrogen, $C_1$–$C_6$-alkyl;

or the agriculturally utilizable salts of the compound I.

The invention further relates to crop protection compositions comprising the compounds I and processes for controlling undesired vegetation with the saccharin derivatives I and use of the compounds I for the production of crop protection compositions having herbicidal action.

WO 96/05182, WO 98/40366 and U.S. Pat. No. 5,801,120 disclose herbicidally active saccharincarbonylcyclohexanedione derivatives.

EP-A 338 992 describes herbicidal benzoyl derivatives which do not have a saccharin structure.

The use of saccharin derivatives as fungicides is furthermore known, e.g. JP Publication 72/00419 and 73/35457 and in pharmacy, e.g. EP-A 594 257.

The herbicidal properties of the known compounds and the compatibility with crop plants are, however, only of limited satisfactoriness.

The object of the present invention is to make available alternative saccharin derivatives having novel structural features. Surprisingly, it has been found that the saccharin derivatives of the formula I have improved properties in comparison with the saccharin derivatives known hitherto.

Compounds of the formula I are obtained according to Scheme 1 by acylating diones of the formula II with a saccharin-5-carbonyl chloride of the formula III and rearranging the enol esters of the formula IV obtained in the presence of a catalyst to give the active compound of the formula I.

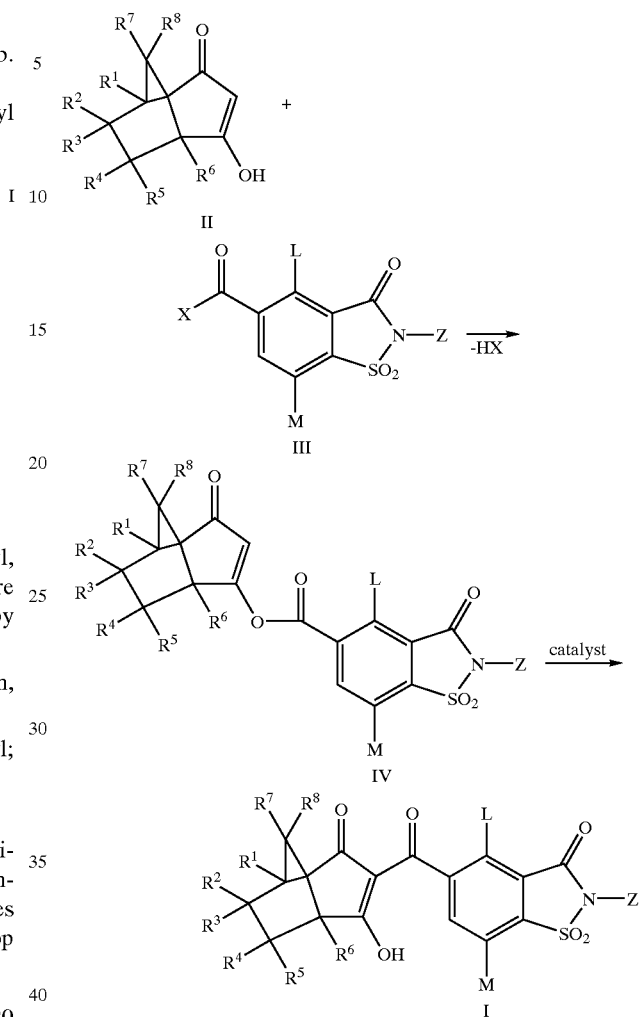

In the above Scheme 1, the substituents $R^1$ to $R^8$, L, M and Z have the meaning given at the outset. X is an easily removable group, such as, for example, halogen, in particular chlorine, or an anhydride group derived from an organic or inorganic acid.

The first step of the reaction sequence in Scheme 1 is carried out by addition of the acid halide III to the solution or suspension of the dione II in the presence of an auxiliary base. The reactants and the auxiliary base are Preferably employed in equimolar amounts, but a small excess of 1.2 to 1.5 molar equivalents of the auxiliary base can be advantageous. Solvents which can be used are methylene chloride, tetrahydrofuran, ethyl acetate, toluene or preferably acetonitrile. Suitable auxiliary bases are alkali metal carbonates, pyridine or tertiary alkylamines, preferably triethylamine. During the addition of the acid chloride, the reaction mixture is preferably cooled to 0 to 10° C., and then it is stirred at a temperature of 20 to 70° C., in particular 25 to 40° C., until the reaction is complete.

The enol ester IV can be isolated before the rearrangement, but the reaction is preferably carried out by adding two to four, preferably 2.5, equivalents of triethylamine to the reaction mixture and then adding 2 to 10, in particular 3, mol % of a cyano compound such as acetone cyanohydrin or preferably trimethylsilyl cyanide at 25° C. and then stirring at a temperature of 20 to 40° C., preferably at 25° C., until the enol ester IV is no longer present. Examples of the cyanide-catalyzed rearrangement of enol esters are found in EP 338 992 and EP 0 252 298.

Working-up is carried out by acidifying the reaction mixture with 5% strength by weight hydrochloric acid or sulfuric acid and then extracting with a solvent such as ethyl acetate or methylene chloride. After drying the extract over sodium sulfate or magnesium sulfate, the solvent is distilled off in vacuo and the crude product is subjected, if necessary, to purification. For purification, the reaction product can be, for example, chromatographed (silica gel, cyclohexane/ethyl acetate) or recrystallized (methanol/water or glacial acetic acid/water). A further purification method is extraction of an ethyl acetate solution of the crude product with an aqueous alkali metal carbonate solution, the final product passing into the aqueous phase. Acidification of the aqueous solution and fresh extraction yields the final product, after drying and removing the solvent, in purer form.

The diones of the formula II used as starting materials are known and can be prepared in a manner known per se [cf. EP-A 338 992; R. Gleiter, Tetrahedron 1980, 36: 655; JP 10,265441; JP 10, 265415].

The acid halides of the formula III used as starting materials are likewise known. If X=Cl, they are obtained by reaction of a suitably substituted saccharin-5-carboxylic acid with thionyl chloride. The synthesis of substituted saccharin-5-carboxylic acids is described, for example, in DE 44 27 996.

In the definition of the various radicals in formula I, the terms indicated are, either per se (such as, for example, $C_1$–$C_6$-"alkyl") or as moieties or in combination with chemical groups of different composition (such as, for example, $C_1$–$C_6$-halo-"alkyl", phenyl-$C_1$–$C_6$-"alkyl"), fundamentally a collective term for a group of compounds. In the case in which the phenyl rings can be mono- or polysubstituted, the substituents can fundamentally be identical or different.

In the definitions of the compounds I given at the beginning, collective terms were used which are generally representative of the following groups:

alkyl: straight-chain or branched alkyl groups having 1 to 6, preferably 1–4, carbon atoms, e.g. $C_1$–$C_4$-alkyl such as methyl, ethyl, propyl, 1-methylethyl, butyl, 1-methylpropyl, 2-methylpropyl and 1,1-dimethylethyl;

alkoxy: straight-chain or branched alkyl groups having 1 to 6, preferably 1–4, carbon atoms as mentioned above, which are bonded to the structure via an oxygen atom (—O—), e.g. $C_1$–$C_3$-alkoxy such as methyloxy, ethyloxy, propyloxy and 1-methylethyloxy;

cycloalkyl: monocyclic alkyl groups having 3 to 8 carbon ring members, e.g. cyclopropyl, cyclobutyl, cyclopentyl, cyclohexyl, cycloheptyl and cyclooctyl;

alkenyl: straight-chain or branched alkenyl groups having 2, preferably 3 to 6, carbon atoms and a double bond in any desired position, e.g. $C_2$–$C_6$-alkenyl such as ethenyl, 1-propenyl, 2-propenyl, 1-methylethenyl, 1-butenyl, 2-butenyl, 3-butenyl, 1-methyl-1-propenyl, 2-methyl-1-propenyl, 1-methyl-2-propenyl, 2-methyl-2-propenyl, 1-pentenyl, 2-pentenyl, 3-pentenyl, 4-pentenyl, 1-methyl-1-butenyl, 2-methyl-1-butenyl, 3-methyl-1-butenyl, 1-methyl-2-butenyl, 2-methyl-2-butenyl, 3-methyl-2-butenyl, 1-methyl-3-butenyl, 2-methyl-3-butenyl, 3-methyl-3-butenyl, 1,1-dimethyl-2-propenyl, 1,2-dimethyl-1-propenyl, 1,2-dimethyl-2-propenyl, 1-ethyl-1-propenyl, 1-ethyl-2-propenyl, 1-hexenyl, 2-hexenyl, 3-hexenyl, 4-hexenyl, 5-hexenyl, 1-methyl-1-pentenyl, 2-methyl-1-pentenyl, 3-methyl-1-pentenyl, 4-methyl-1-pentenyl, 1-methyl-2-pentenyl, 2-methyl-2-pentenyl, 3-methyl-2-pentenyl, 4-methyl-2-pentenyl, 1-methyl-3-pentenyl, 2-methyl-3-pentenyl, 3-methyl-3-pentenyl, 4-methyl-3-pentenyl, 1-methyl-4-pentenyl, 2-methyl-4-pentenyl, 3-methyl-4-pentenyl, 4-methyl-4-pentenyl, 1,1-dimethyl-2-butenyl, 1,1-dimethyl-3-butenyl, 2,1-dimethyl-1-butenyl, 1,2-dimethyl-2-butenyl, 1,2-dimethyl-3-butenyl, 1,3-dimethyl-1-butenyl, 1,3-dimethyl-2-butenyl, 1,3-dimethyl-3-butenyl, 2,2-dimethyl-3-butenyl, 2,3-dimethyl-1-butenyl, 2,3-dimethyl-2-butenyl, 2,3-dimethyl-3-butenyl, 3,3-dimethyl-1-butenyl, 3,3-dimethyl-2-butenyl, 1-ethyl-1-butenyl, 1-ethyl-2-butenyl, 1-ethyl-3-butenyl, 2-ethyl-1-butenyl, 2-ethyl-2-butenyl, 2-ethyl-3-butenyl, 1,1,2-trimethyl-2-propenyl, 1-ethyl-1-methyl-2-propenyl, 1-ethyl-2-methyl-1-propenyl and 1-ethyl-2-methyl-2-propenyl, alkynyl: straight-chain or branched alkynyl groups having 3 to 5 carbon atoms and a triple bond in any desired position, e.g. $C_3$–$C_5$-alkynyl such as 2-propynyl, 2-butynyl, 3-butynyl, 1-methyl-2-propynyl, 2-pentynyl, 3-pentynyl, 4-pentynyl, 1-methyl-2-butynyl, 1-methyl-3-butynyl, 2-methyl-3-butynyl, 1,1-dimethyl-2-propynyl and 1-ethyl-2-propynyl;

halogen: fluorine, chlorine, bromine and iodine; preferably fluorine or chlorine;

haloalkyl: a $C_1$–$C_6$-alkyl radical as mentioned above, which is partially or completely substituted by fluorine, chlorine, bromine and/or iodine, e.g. trichloromethyl, trifluoromethyl, difluoromethyl, 2-fluoroethyl, 2-chloroethyl, 2-bromoethyl, 2,2-difluoroethyl, 2,2,2-trifluoroethyl, 2,2,2-trichloroethyl, 2-fluoropropyl, 3-fluoropropyl, 2-chloropropyl or 3-chloropropyl, in particular trifluoromethyl;

phenylalkyl: a $C_1$–$C_6$-alkyl radical as mentioned above, which is substituted by phenyl in any desired position, in particular benzyl, 2-phenylethyl.

Phenyl rings may, in principle, be unsubstituted or substituted. Substituted phenyl rings are preferably mono-, di- or trisubstituted by alkyl, alkoxy or halogen. The substituents may be in the 2-, 3- or 4-position. In the case of monosubstituted phenyl rings, preference is given to the 2- or 4-position, and, in the case of disubstituted phenyl rings, preference is given to the 2,4-position.

With respect to the intended use as herbicides, saccharin-5-carbonyl derivatives of the formula I are preferred where the following radicals per se or in combination with one another have the following meanings in particular:

1. L: $C_1$–$C_3$-alkyl, such as, for example, methyl, ethyl; $C_1$–$C_3$-alkoxy, such as, for example, methoxy, ethoxy; in particular methyl.
2. Z: $C_1$–$C_4$-alkyl, $C_3$–$C_8$-cycloalkyl, $C_3$–$C_6$-alkenyl, $C_3$–$C_5$-alkynyl, benzyl and phenyl.
3. Z as under item 2, in particular methyl, ethyl, i-propyl, i-butyl, t-butyl, cyclopropyl; cyclohexyl, allyl, propargyl, phenyl and benzyl; particularly preferably methyl, ethyl and phenyl and very particularly preferably methyl.
4. M: hydrogen, $C_1$–$C_4$-alkyl, $C_1$–$C_4$-alkoxy, fluoro, chloro, cyano, nitro, halo-$C_1$–$C_4$-alkyl.
5. M as under item 4, in particular methyl, ethyl, methoxy, ethoxy, fluoro, chloro, cyano, nitro and trifluoromethyl.
6. M as under item 4 or 5, preferably hydrogen, methyl, ethyl, methoxy and chlorine; particularly preferably hydrogen, methyl and chlorine.

7. $R^1, R^2, R^3, R^4, R^5, R^6, R^7, R^8$ : hydrogen, $C_1$–$C_3$-alkyl. Preferably, 5–8 of the radicals $R^1$–$R^8$ are hydrogen and up to three radicals are alkyl, in particular methyl.

8. $R^7$ and $R^8$ are preferably identical and are in particular hydrogen or methyl.

Preferred compounds are also those of the formulae I, II, III and IV which result from single or multiple combinations of the meanings mentioned under items 1.–8.

Very particularly preferred saccharin derivatives of the formula I are those in which the substituents contain one or more of the following features:

1. L: methyl.
2. $R^1$–$R^8$: in each case hydrogen.
3. Z: methyl.
4. M: hydrogen, methyl or chlorine.

The compounds I can be present in the form of their agriculturally utilizable salts, where the nature of the salts in general does not matter. Customarily, the salts of those bases will be suitable which do not adversely affect the herbicidal action of I.

Suitable basic salts are particularly those of the alkali metals, preferably the lithium, sodium and potassium salts, those of the alkaline earth metals, preferably calcium, magnesium and barium salts and those of the transition metals, preferably manganese, copper, zinc and iron salts, ammonium salts, and also ammonium salts which can carry one to four $C_1$–$C_4$-alkyl, or hydroxy-$C_1$–$C_4$-alkyl substituents, a phenyl or benzyl substituent, preferably diethylammonium, diisopropylammonium, tetramethylammonium, tetrabutylammonium, trimethylbenzylammonium, and trimethyl(2-hydroxyethyl)ammonium salts, the phosphonium salts, the sulfonium salts, preferably tri-($C_1$–$C_4$)alkyl sulfonium salts, and the sulfoxonium salts, preferably tri-($C_1$–$C_4$)alkylsulfoxonium salts.

The compounds I and their agriculturally utilizable salts are suitable—both as isomer mixtures and in the form of the pure isomers—as herbicides. The herbicidal compositions comprising I control vegetation on uncultivated areas very well, particularly at high application rates. In crops such as wheat, rice, corn, soybeans and cotton, they act against broad-leaved weeds and grass weeds without noticeably damaging the crop plants. This effect occurs especially at low application rates.

Depending on the particular application method, the compounds I or compositions comprising them can additionally be employed in a further number of crop plants for eliminating undesired plants. Suitable crops are, for example, the following:

*Allium cepa, Ananas comosus, Arachis hypogaea, Asparagus officinalis, Beta vulgaris* spec. *altissima, Beta vulgaris* spec. *rapa, Brassica napus* var. *napus, Brassica napus* var. *napobrassica, Brassica rapa* var. *silvestris, Camellia sinensis, Carthamus tinctorius, Carya illinoinensis, Citrus limon, Citrus sinensis, Coffea arabica (Coffea canephora, Coffea liberica), Cucumis sativus, Cynodon dactylon, Daucus carota, Elaeis guineensis, Fragaria vesca, Glycine max, Gossypium hirsutum, (Gossypium arboreum, Gossypium herbaceum, Gossypium vitifolium), Helianthus annuus, Hevea brasiliensis, Hordeum vulgare, Humulus lupulus, Ipomoea batatas, Juglans regia, Lens culinaris, Linum usitatissimum, Lycopersicon lycopersicum,* Malus spec., *Manihot esculenta, Medicago sativa,* Musa spec., *Nicotiana tabacum (N.rustica), Olea europaea, Oryza sativa, Phaseolus lunatus, Phaseolus vulgaris, Picea abies,* Pinus spec., *Pisum sativum, Prunus avium, Prunus persica, Pyrus communis, Ribes sylvestre, Ricinus communis, Saccharum officinarum, Secale cereale, Solanum tuberosum, Sorghum bicolor (S. vulgare), Theobroma cacao, Trifolium pratense, Triticum aestivum, Triticum durum, Vicia faba, Vitis vinifera, Zea mays.*

Moreover, the compounds I can also be used in crops which have been made tolerant to the action of herbicides by means of breeding, including genetic engineering methods.

The herbicidal compositions or the active compounds can be applied preemergence or postemergence. If the active compounds are less tolerable to certain crop plants, application techniques can be used in which the herbicidal compositions are sprayed with the aid of the spray equipment such that the leaves of the sensitive crop plants are not affected if possible, while the active compounds reach the leaves of undesired plants growing under them or the uncovered soil surface (post-directed, lay-by).

The compounds I and the herbicidal compositions comprising them can be applied by spraying, atomizing, dusting, broadcasting or watering, for example in the form of directly sprayable aqueous solutions, powders, suspensions, also high-percentage aqueous, oily or other suspensions or dispersions, emulsions, oil dispersions, pastes, dusting agents, broadcasting agents or granules. The application forms depend on the intended use; if possible they should in each case guarantee the finest distribution of the active compounds according to the invention.

Suitable inert additives are mainly: mineral oil fractions of medium to high boiling point, such as kerosene, or diesel oil, furthermore coal tar oils and oils of vegetable or animal origin, aliphatic, cyclic and aromatic hydrocarbons, e.g. paraffin, tetrahydronaphthalene, alkylated naphthalenes or their derivatives, alkylated benzenes or their derivatives, alcohols such as methanol, ethanol, propanol, butanol, cyclohexanol, ketones such as cyclohexanone or strongly polar solvents, e.g. amines, such as N-methylpyrrolidone or water.

Aqueous application forms can be prepared from emulsion concentrates, suspensions, pastes, wettable powders or water-dispersible granules by addition of water. For the preparation of emulsions, pastes or oil dispersions, the saccharin-5-carbonyl derivatives can be homogenized in water, as such or dissolved in an oil or solvent, by means of wetting agents, adherents, dispersants or emulsifiers. However, concentrates consisting of active substance, wetting agent, adherent, dispersant or emulsifier and possibly solvent or oil can also be prepared, which are suitable for dilution with water.

Suitable surface-active substances are the alkali metal, alkaline earth metal and ammonium salts of aromatic sulfonic acids, e.g. ligno-, phenol-, naphthalene- and dibutyl-naphthalenesulfonic acid, and also of fatty acids, alkyl and alkylaryl sulfonates, alkyl, lauryl ether and fatty alcohol sulfates, as well as salts of sulfated hexa-, hepta- and octadecanols, and also of fatty alcohol glycol ethers, condensation products of sulfonated naphthalene and its derivatives with formaldehyde, condensation products of naphthalene or of the naphthalenesulfonic acids with phenol and formaldehyde, polyoxyethylene octylphenyl ethers, ethoxylated isooctyl, octyl- or nonylphenyl, alkylphenyl or tributylphenyl polyglycol ethers, alkylaryl polyether alcohols, isotridecyl alcohol, fatty alcohol-ethylene oxide condensates, ethoxylated castor oil, polyoxyethylene alkyl ethers or polyoxypropylene alkyl ethers, lauryl alcohol polyglycol ether acetate, sorbitol esters, lignin-sulfite waste liquors or methylcellulose.

Powder compositions, broadcasting compositions and dusting compositions can be prepared by mixing or joint grinding of the active substances with a solid carrier.

Granules, e.g. coated, impregnated and homogeneous granules, can be prepared by binding the active compounds to solid carriers. Solid carriers are mineral earths such as silicic acids, silica gels, silicates, talc, kaolin, limestone, lime, chalk, bole, loess, clay, dolomite, diatomaceous earth, calcium sulfate and magnesium sulfate, magnesium oxide, ground synthetic materials, fertilizers, such as ammonium sulfate, ammonium phosphate, ammonium nitrate, ureas and plant products such as cereal flour, tree bark meal, wood meal and nutshell meal, cellulose powder or other solid carriers.

The concentrations of the active compounds I in the ready-to-use preparations can be varied within wide ranges. The formulations in general contain 0.001 to 98% by weight, preferably 0.01 to 95% by weight, of at least one active compound. The active compounds are employed here in a purity of 90% to 100%, preferably 95% to 100% (according to NMR spectrum).

The compounds I according to the invention can be formulated, for example, as follows:

I 20 parts by weight of a compound of the formula I are dissolved in a mixture which consists of 80 parts by weight of alkylated benzene, 10 parts by weight of the addition product of 8 to 10 mol of ethylene oxide to 1 mol of oleic acid N-monoethanolamide, 5 parts by weight of calcium salt of dodecylbenzenesulfonic acid and 5 parts by weight of the addition product of 40 mol of ethylene oxide to 1 mol of castor oil. By pouring out and finely dispersing the solution in 100,000 parts by weight of water, an aqueous dispersion is obtained which contains 0.02% by weight of the active compound.

II 20 parts by weight of a compound of the formula I are dissolved in a mixture which consists of 40 parts by weight of cyclohexanone, 30 parts by weight of isobutanol, 20 parts by weight of the addition product of 7 mol of ethylene oxide to 1 mol of isooctylphenol and 10 parts by weight of the addition product of 40 mol of ethylene oxide to 1 mol of castor oil. By pouring the solution into and finely dispersing it in 100,000 parts by weight of water, an aqueous dispersion is obtained which contains 0.02% by weight of the active compound.

III 20 parts by weight of a compound of the formula I are dissolved in a mixture which consists of 25 parts by weight of cyclohexanone, 65 parts by weight of a mineral oil fraction of boiling point 210 to 280° C. and 10 parts by weight of the addition product of 40 mol of ethylene oxide to 1 mol of castor oil. By pouring the solution into and finely dispersing it in 100,000 parts by weight of water, an aqueous dispersion is obtained which contains 0.02% by weight of the active compound.

IV 20 parts by weight of a compound of the formula I are well mixed with 3 parts by weight of the sodium salt of diisobutylnaphthalenesulfonic acid, 17 parts by weight of the sodium salt of a lignosulfonic acid from a sulfite waste liquor and 60 parts by weight of powdered silica gel and ground in a hammer mill. By finely dispersing the mixture in 20,000 parts by weight of water, a spray mixture is obtained which contains 0.1% by weight of the active compound.

V 3 parts by weight of a compound of the formula I are mixed with 97 parts by weight of finely divided kaolin. In this way, a dusting agent is obtained which contains 3% by weight of the active compound.

VI 20 parts by weight of a compound of the formula I are intimately mixed with 2 parts by weight of calcium salt of dodecylbenzenesulfonic acid, 8 parts by weight of fatty alcohol polyglycol ether, 2 parts by weight of sodium salt of a phenol/urea/formaldehyde condensate and 68 parts by weight of a paraffinic mineral oil. A stable oily dispersion is obtained.

VII 1 part by weight of a compound of the formula I is dissolved in a mixture which consists of 70 parts by weight of cyclohexanone, 20 pares by weight of ethoxylated isooctylphenol and 10 parts by weight of ethoxylated castor oil. A stable emulsion concentrate is obtained.

VIII 1 part by weight of a compound of the formula I is dissolved in a mixture which consists of 80 parts by weight of cyclohexanone and 20 parts by weight of Wettol ® EM 31 (nonionic emulsifier based on ethoxylated castor oil). A stable emulsion concentrate is obtained.

To broaden the spectrum of action and to achieve synergistic effects, the saccharin-5-carbonyl derivatives of the formula I or the crop protection compositions comprising this compound can be combined with numerous representatives of other herbicidal or growth-regulating groups of active compounds and applied together or separately. For example, suitable mixture components are 1,2,4-thiadiazoles, 1,3,4-thiadiazoles, amides, aminophosphoric acid and its derivatives, aminotriazoles, anilides, (het) aryloxyalkanoic acid and its derivatives, benzoic acid and its derivatives, benzothiadiazinones, 2-aroyl-1,3-cyclohexanediones, hetaryl aryl ketones, benzylisoxazolidinones, meta-$CF_3$-phenyl derivatives, carbamates, quinolinecarboxylic acid and its derivatives, chloroacetanilides, cyclohexane-1,3-dione derivatives, diazines, dichloropropionic acid and its derivatives, dihydrobenzofurans, dihydrofuran-3-ones, dinitroanilines, dinitrophenols, diphenyl ethers, dipyridyls, halocarboxylic acids and their derivatives, ureas, 3-phenyluracils, imidazoles, imidazolinones, N-phenyl-3,4,5,6-tetrahydrophthalimides, oxadiazoles, oxiranes, phenols, aryloxy- or heteroaryloxyphenoxypropionic acid esters, phenylacetic acid and its derivatives, phenylpropionic acid and its derivatives, pyrazoles, phenylpyrazoles, pyridazines, pyridinecarboxylic acid and its derivatives, pyrimidyl ethers, sulfonamides, sulfonylureas, triazines, triazinones, triazolinones, triazolecarboxamides and uracils.

Moreover, it may be of benefit to apply the compounds I on their own or in combination with other herbicides and/or mixed with further crop protection agents, for example with agents for controlling pests or phytopathogenic fungi or bacteria, the compounds being applied jointly or separately with these. Furthermore of interest is the miscibility with mineral salt solutions, which are employed for the elimination of nutritional and trace element deficiencies. Nonphytotoxic oils and oil concentrates can also be added.

Depending on the control target, time of year, target plants and stage of growth, the application rates of active compound are 0.001 to 3.0, preferably 0.01 to 1.0, kg/ha of active substance (a.s.).

EXAMPLE 1

Active compound from bicyclo[3.2.]oct-3-en-2-one and 2,4-dimethylsaccharin-5-carbonyl chloride (No. 1.1 in Table 1)

3.03 g (0.22 mol) of bicyclo[3.2.1]oct-3-en-2-one and 6.10 g (0.022 mol) of 2,4-dimethylsaccharin-5-carbonyl chloride are suspended in 100 ml of methylene chloride and 2.43 g (0.024 mol) of triethylamine are added. The mixture is additionally stirred at 25° C. for 2 hours, concentrated and the residue is chromatographed on silica gel (methylene chloride/ethyl acetate 8:2). The enol ester is then dissolved in 300 ml of acetonitrile and treated with 4.80 g (0.047 mol) of triethylamine and 0.3 g (0.003 mol) of trimethylsilyl cyanide. It is stirred at 25° C. overnight, concentrated, the residue is taken up with ethyl acetate, and the mixture is washed with dilute hydrochloric acid, dried and concentrated again. The residue is digested with methanol and filtered off with suction. 6.0 g (73% yield) of a white solid having a melting point of>220° C. are obtained In the same manner, the following compounds in Table 1 can be obtained:

TABLE 1

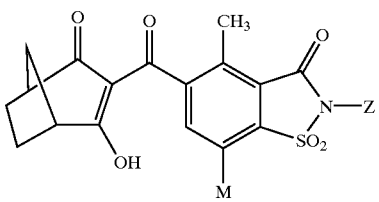

I.A

| Current No. | M | Z | ν |
|---|---|---|---|
| 1.1. | H | CH$_3$ | IR: ν [cm$^{-1}$]: 1724, 1676 |
| 1.2. | H | C$_2$H$_5$ | IR: ν [cm$^{-1}$]: 1728, 1672 |
| 1.3. | H | n-C$_3$H$_7$ | |
| 1.4. | H | i-C$_3$H$_7$ | |
| 1.5. | H | n-C$_4$H$_9$ | |
| 1.6. | H | i-C$_4$H$_9$ | |
| 1.7. | H | s-C$_4$H$_9$ | |
| 1.8. | H | t-C$_4$H$_9$ | |
| 1.9. | H | cyclopropyl | |
| 1.10. | H | cyclobutyl | |
| 1.11. | H | cyclopentyl | |
| 1.12. | H | cyclohexyl | |
| 1.13. | H | allyl | |
| 1.14. | H | propargyl | |
| 1.15. | H | benzyl | |
| 1.16. | H | phenyl | |
| 1.17. | H | 4-Cl-phenyl | |
| 1.18. | H | 2,4-dichlorophenyl | |
| 1.19. | H | 4-methylphenyl | |
| 1.20. | H | 4-methoxyphenyl | |
| 1.21. | CH$_3$ | CH$_3$ | |
| 1.22. | CH$_3$ | C$_2$H$_5$ | |
| 1.23. | CH$_3$ | n-C$_3$H$_7$ | |
| 1.24. | CH$_3$ | i-C$_3$H$_7$ | |
| 1.25. | CH$_3$ | n-C$_4$H$_9$ | |
| 1.26. | CH$_3$ | i-C$_4$H$_9$ | |
| 1.27. | CH$_3$ | s-C$_4$H$_9$ | |
| 1.28. | CH$_3$ | t-C$_4$H$_9$ | |
| 1.29. | CH$_3$ | cyclopropyl | |
| 1.30. | CH$_3$ | cyclobutyl | |
| 1.31. | CH$_3$ | cyclopentyl | |
| 1.32. | CH$_3$ | cyclohexyl | |
| 1.33. | CH$_3$ | allyl | |
| 1.34. | CH$_3$ | propargyl | |
| 1.35. | CH$_3$ | benzyl | |
| 1.36. | CH$_3$ | phenyl | |
| 1.37. | CH$_3$ | 4-Cl-phenyl | |
| 1.38. | CH$_3$ | 2,4-dichlorophenyl | |
| 1.39. | CH$_3$ | 4-methylphenyl | |
| 1.40. | CH$_3$ | 4-methoxyphenyl | |
| 1.41. | Cl | CH$_3$ | |
| 1.42. | Cl | C$_2$H$_5$ | |
| 1.43. | Cl | n-C$_3$H$_7$ | |
| 1.44. | Cl | i-C$_3$H$_7$ | |
| 1.45. | Cl | n-C$_4$H$_9$ | |

TABLE 1-continued

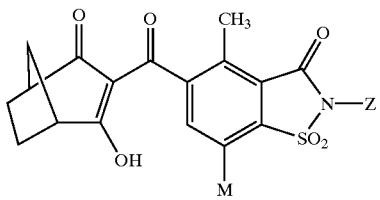

I.A

| Current No. | M | Z | ν |
|---|---|---|---|
| 1.46. | Cl | i-C$_4$H$_9$ | |
| 1.47. | Cl | s-C$_4$H$_9$ | |
| 1.48. | Cl | t-C$_4$H$_9$ | |
| 1.49. | Cl | cyclopropyl | |
| 1.50. | Cl | cyclobutyl | |
| 1.51. | Cl | cyclopentyl | |
| 1.52. | Cl | cyclohexyl | |
| 1.53. | Cl | allyl | |
| 1.54. | Cl | propargyl | |
| 1.55. | Cl | benzyl | |
| 1.56. | Cl | phenyl | |
| 1.57. | Cl | 4-Cl-phenyl | |
| 1.58. | Cl | 2,4-dichlorophenyl | |
| 1.59. | Cl | 4-methylphenyl | |
| 1.60. | Cl | 4-methoxyphenyl | |
| 1.61. | H | CH$_3$ | Na salt; IR: ν [cm$^{-1}$]: 1730, 1647 |
| 1.62. | H | CH$_3$ | K salt; IR: ν [cm$^{-1}$]: 1728, 1645 |
| 1.63. | H | CH$_3$ | Mg salt |
| 1.64. | H | CH$_3$ | Ca salt |
| 1.65. | H | CH$_3$ | Li salt; IR: ν [cm$^{-1}$]: 1730, 1647 |
| 1.66. | H | CH$_3$ | Zn salt |
| 1.67. | H | CH$_3$ | NH$_4$ salt |
| 1.68. | H | CH$_3$ | NHEt$_2$ salt |
| 1.69. | H | CH$_3$ | NEt$_3$ salt |
| 1.70. | H | CH$_3$ | H$_2$N-iPr salt |

In the same manner, the following compounds I. B. in Table 2 can be obtained, where M and Z have the meanings indicated in Table 1:

Table 2:

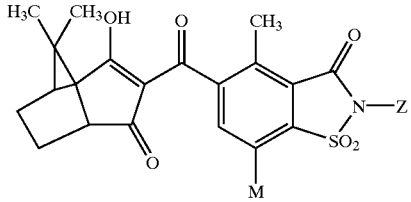

I.B

R$^1$ - R$^6$ = hydrogen; R$^7$, R$^8$ = methyl.

In the same manner, the following compounds I.C. in Table 3 can be obtained, where M and Z have the meanings indicated in Table 1:

Table 3:

I.C

R¹ - R⁵ = hydrogen; R⁶ - R⁸ = methyl.

EXAMPLE 2

It was possible to show the herbicidal action of the saccharin-5-carbonyl derivatives of the formula I by means of greenhouse tests:

The cultivation containers used were plastic pots containing loamy sand with approximately 3.0% humus as a substrate. The seeds of the test plants were sown separately according to species.

In the case of preemergence treatment, the active compounds suspended or emulsified in water were applied directly after sowing by means of finely dispersing nozzles. The containers were lightly watered in order to promote germination and growth, and then covered with transparent plastic hoods until the plants had taken root. This covering causes uniform germination of the test plants if this is not adversely affected by the active compounds. The application rate for preemergence treatment was 0.125 or 0.0625 kg/ha of a.s.

For the purpose of postemergence treatment, the test plants were each first raised to a growth height of 3 to 15 cm, according to growth form, and then treated with the active compounds suspended or emulsified in water. For this, the test plants were either sown directly and grown in the same containers or they were first raised separately as seed plants and transplanted into the test containers a few days before the treatment.

The plants were kept species-specifically at temperatures of 10–25° C. or 20–35° C. The test period extended over 2 to 4 weeks. During this time, the plants were tended, and their reaction to the individual treatments was assessed.

Assessment was carried out on a scale from 0 to 100. In this case, 100 means no emergence of the plants or complete destruction at least of the above-ground parts and 0 means no damage or a normal course of growth.

The plants used in the greenhouse tests were made up of the following species:

| Botanical name | Common name |
| --- | --- |
| Glycine max (GLXMA) | soybean |
| Chenopodium album (CHEAL) | lambsquarter |
| digitaria sanguinalis (DIGSA) | crabgrass, large |
| Echinochloa crus galli (ECHCG) | barnyard grass, common |
| Setaria viridis (SETVI) | foxtail, green |

Preemergence, weed grasses and broad-leaved plants are very well controlled using the compound 1.1 at 0.125 and 0.0625 kg/ha a.s.

Table 1: Selective activity when used preemergence in the greenhouse

Compound according to Example No. 1.1.

| Test plants | Application rates (kg/ha of a.s.) 0.125 | Application rates (kg/ha of a.s.) 0.0625 |
| --- | --- | --- |
| GLXMA | 0 | 0 |
| CHEAL | 98 | 98 |
| DIGSA | 98 | 98 |
| ECHCG | 98 | 98 |
| SETVI | 100 | 98 | a.s. = active substance

We claim:
1. A saccharin-5-carbonyl derivative of the formula I

I in which the substituents have the following meanings:
L is $C_1$–$C_5$-alkyl, $C_1$–$C_6$-alkoxy;
Z is $C_1$–$C_6$-alkyl, $C_3$–$C_8$-cycloalkyl, $C_3$–$C_6$-alkenyl, $C_3$–$C_5$-alkynyl, phenyl-$C_1$–$C_6$-alkyl or phenyl, where the phenyl rings can be mono- or polysubstituted by $C_1$–$C_6$-alkyl, $C_1$–$C_6$-alkoxy or halogen;
M is hydrogen, $C_1$–$C_6$-alkyl, $C_1$–$C_6$-alkoxy, halogen, cyano, nitro or halo-$C_1$–$C_6$-alkyl;
$R^1$, $R^2$, $R^3$, $R^4$, $R^5$, $R^6$, $R^7$, $R^8$ are hydrogen or $C_1$–$C_6$-alkyl;
or the agriculturally utilizable salts of the compound I.
2. A saccharin derivative of the formula I as claimed in claim 1, in which L is methyl, ethyl, methoxy or ethoxy.
3. A saccharin derivative of the formula I as claimed in claim 1, in which Z is $C_1$–$C_4$-alkyl, $C_3$–$C_8$-cycloalkyl, $C_3$–$C_6$-alkenyl, $C_3$–$C_5$-alkynyl, phenyl or benzyl.
4. A saccharin derivative of the formula I as claimed in claim 1, in which Z is methyl, ethyl, i-propyl, i-butyl, t-butyl, cyclopropyl, cyclohexyl, allyl, propargyl, phenyl or benzyl.
5. A saccharin derivative of the formula I as claimed in claim 1, in which M is hydrogen, methyl, ethyl, methoxy, ethoxy, fluoro, chloro, cyano, nitro or trifluoromethyl.
6. A saccharin derivative of the formula I as claimed in claim 1, in which M is hydrogen, methyl, ethyl, methoxy or chloro.
7. A saccharin derivative of the formula I as claimed in claim 1, in which $R^1$ to $R^8$ are hydrogen.
8. A saccharin derivative of the formula I as claimed in claim 1, in which one, two or three of the radicals $R^1$ to $R^8$ is/are methyl, ethyl, n-propyl or n-butyl, and the remaining radicals are hydrogen.

9. A saccharin derivative of the formula I as claimed in claim 1, where $R^7$ and $R^8$ are identical and are hydrogen or methyl.

10. A saccharin derivative of the formula I as claimed in claim 1, where $R^6$ is hydrogen or methyl.

11. A crop protection composition comprising at least one saccharin derivative of the formula I as claimed in claim 1 and customary inert additives.

12. A crop protection composition as claimed in claim 11 having herbicidal or growth-regulating action.

13. A process for the treatment of plants for controlling undesired growth of harmful plants, which comprises bringing the plants or their habitat into contact with an effective amount of a compound of the formula I as claimed in claim 1 or a composition comprising this compound.

14. A process for controlling undesired vegetation, which comprises allowing a herbicidally effective amount of a compound of the formula I according to claim 1 to act on the plants or their habitat.

15. A process for preparing crop protection compositions as claimed in claim 11, which comprises mixing at least one compound of the formula I with inert additives and processing the mixture into suitable application forms as crop protection compositions.

* * * * *